United States Patent

Werner et al.

Patent Number: 5,407,425
Date of Patent: Apr. 18, 1995

[54] SYSTEM FOR THE COLLECTING AND RETRANSFUSION OF AUTOLOGOUS BLOOD

[76] Inventors: Margrit Werner, Lion-Feuchtsheim-Str. 69, 6500 Mainz-Hechtsheim; Klaus-Hermann Schütt, Schillerstr. 34, 6501 Budenheim, both of Germany

[21] Appl. No.: 297,922

[22] Filed: Aug. 31, 1994

Related U.S. Application Data

[63] Continuation of Ser. No. 629,579, Dec. 18, 1990, abandoned.

[30] Foreign Application Priority Data

Dec. 29, 1989 [DE] Germany .................. 39 43 300.5

[51] Int. Cl.⁶ ............................................. A61M 37/00
[52] U.S. Cl. ............................................. 604/4; 604/7; 604/5
[58] Field of Search ............... 604/4, 5, 6, 269, 408, 604/411, 415, 416, 7, 19, 27, 28, 30; 210/651

[56] References Cited

U.S. PATENT DOCUMENTS

| | | | |
|---|---|---|---|
| 3,545,671 | 12/1970 | Ross | 233/26 |
| 4,040,959 | 8/1977 | Berman et al. | 210/78 |
| 4,333,016 | 6/1982 | Bilstad et al. | 250/577 |
| 4,428,744 | 1/1984 | Edelson | 604/6 |
| 4,439,190 | 3/1984 | Protzmann et al. | 604/319 |
| 4,540,406 | 9/1985 | Miles | 604/6 |
| 4,547,186 | 10/1985 | Bartlett | 604/4 |
| 4,551,131 | 11/1985 | Miles et al. | 604/269 |
| 4,655,742 | 4/1987 | Vantard | 604/6 |
| 4,668,214 | 5/1987 | Reeder | 494/37 |
| 4,687,580 | 8/1987 | Malbrancq et al. | 604/6 |
| 4,842,576 | 6/1989 | Lysacht et al. | 604/6 |
| 4,850,998 | 7/1989 | Schoendorfer | 604/28 |
| 5,055,198 | 10/1991 | Shettigar | 604/28 |

FOREIGN PATENT DOCUMENTS

| | | |
|---|---|---|
| 2627134A1 | 12/1977 | Germany . |
| 3012227 | 10/1980 | Germany . |
| 3448173 | 11/1984 | Germany . |
| 3524552A1 | 1/1986 | Germany . |
| 3441891C2 | 5/1986 | Germany . |
| 2135890 | 9/1984 | United Kingdom . |
| 2139094 | 11/1984 | United Kingdom . |

OTHER PUBLICATIONS

Kron, W. M., "Autotransfusion–When and How", Medical Corps International Apr. 1987 pp. 25–27.
Prospectus of "Solcotrans-System".
Schmidt, R. et al, Eine neue Method . . . Angio 5, Nr. 1, pp. 31–34 (1983).

*Primary Examiner*—Sam Rimell
*Attorney, Agent, or Firm*—Wigman, Cohen, Leitner & Myers

[57] ABSTRACT

In a closed system for collecting and retransfusing autologous blood having a collecting vessel (4) to receive the blood and an anticoagulant fluid, as well as a retransfusion line (14, 14') containing a microfilter, through which at least a portion of the blood collected in the collecting vessel (4) is retransfused, the inlet for the anticoagulant fluid is provided, preferably between the collecting vessel (4) in which a negative pressure can be maintained and a drain (2) or the open end of a drain tube. The collecting vessel (4) is connected with a collecting and separating container (13, 13') by means of a tube line (10, 10'), to which a tube pump (11) can be applied. The retransfusion line (14, 14') for the erythrocyte concentrate deposited in the collecting and separating container (13, 13') is connected to the outlet thereof.

24 Claims, 2 Drawing Sheets

SYSTEM FOR THE COLLECTING AND RETRANSFUSION OF AUTOLOGOUS BLOOD

This is a continuation of application Ser. No. 07/629,579, filed on Dec. 18, 1990, now abandoned.

BACKGROUND OF THE INVENTION

1. Field of the Invention

The invention relates to a system for the collection and retransfusion of autologous blood.

2. Description of the Prior Art

In a known system of this type, namely the "solcotransystem," the collecting vessel for the drainage blood consists of a bag arranged inside a rigid plastic bottle which can be evacuated to produce a negative pressure in the bag and to maintain this negative pressure for a certain period of time. A given amount of an anticoagulant is placed in the bag before the blood is introduced. When the bag is filled to the desired level, it is separated from the tube leading from it to the drain, so that its contents can be retransfused to the patient through a microfilter.

One disadvantage of this conventional system is that, depending on the wound conditions, a varying degree of hemolysis can arise, which leads to substantial fluctuations in the quality of the erythrocytes to be retransfused. An additional disadvantage is that the blood is subjected to a relatively long contact with a foreign surface before it can be mixed with the anticoagulant fluid in the collecting bottle. This leads to an activation of clotting factors as well as the kinin and complement systems. The activation of the Ca-dependent clotting factors is not interrupted until the blood comes into contact with the anticoagulant fluid stabilizer. Adequate mixing of the blood with the anticoagulant is only assured if the two fluids are repeatedly mechanically mixed, which is a further disadvantage of the known system. Aside from activated clotting factors, the blood contained in the collecting vessel also contains fat and fatty tissue from the area of the wound. Although the blood is mechanically filtered by the microfilter prior to transfusion, small clots, less than 40 $\mu$l in size, of fat and activated clotting factors nevertheless can enter the circulatory system of the patient, so that the risk of thromboembolic complications and fat embolisms cannot be precluded, which is extremely disadvantageous.

Another known system is free of this last disadvantage. In this conventional system the blood is subjected to a washing process using a physiological common salt solution to remove the fat and clotting factors. However, this system is very expensive and personnel-intensive in operation, which is why it is only employed in large clinics. In addition, both of these known systems are open, so that the risk of contamination exists.

OBJECTS AND SUMMARY OF THE INVENTION

A principal object of the present invention is to provide a system for collecting and retransfusing autologous blood, which overcomes the disadvantages of conventional systems. Another object of the present invention is to provide a system for collecting and transfusing autologous blood which can be employed where the known bloodwashing system, as noted above, cannot, due to expense and personnel requirements. These objects and other objects are achieved by providing an improved system for collecting and retransfusing autologous blood comprising:

a) a collecting vessel to receive blood and anticoagulant fluid, said collecting vessel being connected to a tube in which negative pressure can be maintained;

b) a transfusion line containing a microfilter through which at least a portion of the blood collected in the collecting vessel is retransfused;

c) means for introducing the anticoagulant fluid into the blood before entering the collecting vessel;

d) a collecting and separating bag for receiving the erythrocyte concentrate fluidly connected to said collecting vessel by means of a tube line, the outlet of said collecting and separating bag being fluidly connected to a retransfusion line.

The closed blood collection and retransfusion system according to the invention, i.e., one which precludes the introduction of germs, prevents any risk of contamination. The fact that the blood is mixed with the anticoagulation fluid prior to entering the collecting vessel achieves, first of all, an automatic and thorough mixing, and secondly, reduces to a minimum the amount of time in which the blood is in contact with a foreign surface. It is also advantageous that the effective negative pressure in the collecting vessel can be controlled by means of the tube pump, and can thereby be held at an optimum value.

Another significant advantage of the present invention is achieved by means of the collecting and separating container in that, solely by the force of gravity, a separation of the blood into erythrocyes and plasma components takes place within a relatively short time. It is therefore possible to retransfuse only the erythrocyte concentrate to the patient through the retransfusion line.

In addition, this system is also suitable to perform plasma and erythrocyte apheresis for patients with, for example, hyperviscosity syndrome, autoimmune system illnesses and hemochromatosis or polycythemia. In the plasma apheresis, the patient receives, after sedimentation of the blood, his own erythrocytses retransfused, and the plasma is disposed of via a connected collecting vessel. In the erythrocyte aspheresis the erythrocyte concentrate is disposed of and the plasma is retransfused.

The separation of the erythrocytes from the plasma components can be accelerated by the addition to the anticoagulating fluid of at least one substance which accelerates the precipitation of the erythrocytes, such as, for example, hydroxyethyl starch. The system according to the present invention eliminates the need to wait until large quantities of blood are available. After just a relatively short time retransfusion can begin, whereby fully active erythrocytes can be retransfused. In this manner, an erythrocyte concentrate with a high hematocrit can be transfused with practically no risk for the patient. Since collection and retransfusions can be carried out without opening the system by disconnections or reconnections, accidental germ introduction is prevented, thereby avoiding the risks associated with the known systems. Finally, the system according to the invention also offers the advantage that it can be used not only for post operative aspiration with retransfusion, but also for wound drainage and for interoperative aspiration. In the latter case, if aspiration takes place only at the end opening of the drain, it is sufficient simply to place a grommet-like sleeve on the drain This sleeve is then removed before the wound is closed.

It is preferable to connect a drip element with the inlet for the anticoagulant by means of a tube, which drip element contains the supply of anticoagulant fluid, if necessary mixed with at least one substance to accelerate precipitation. This drip element preferably includes a quantity dosing device which can be controlled by a sensor which detects the quantity of blood flowing into the collecting vessel and controls the admixture of the anticoagulant fluid in dependence on volume. This sensor can be arranged at the entrance to the collecting vessel or earlier in the system. However, the blood can also be introduced into the collecting vessel by means of drip element and can adjust the quantity dosing device for the anticoagulant fluid depending on its quantity setting.

The collecting vessel, in one preferred embodiment, is a rigid container, so that the desired negative pressure can be easily maintained therein using a tube pump in contact with the tube leading from the collecting vessel to the collecting and separating container or bag. The tube pump can be controlled in accordance with the desired negative pressure prevailing in the collecting vessel. In one preferred embodiment, the collecting vessel includes a negative pressure display device. This negative pressure display device can generate a visual indication or an acoustic signal, so that the tube pump is activated when it is not continuously turned on.

In one preferred embodiment, the collecting and separating container includes a separation zone, in which the upper portion, to which the tube line is connected, can be tightly closed against the lower portion, to which the retransfusion line is connected. The erythrocyte concentrate collected in the lower portion can then be removed without the danger of the plasma located in the upper portion being removed. The separation in the separating zone can, for example, be undertaken with a clamping device which is installed externally. However, a welded element can be provided in the separating zone if the quantity of erythrocyte concentrate available after the first collection is sufficient for the retransfusion. The collecting and separating container is therefore preferably a bag made from a soft and, if necessary, weldable plastic. In addition, instead of arranging a separating means at the outlet, a sensor can be arranged which detects whether erythrocytes or plasma are flowing out and then, when it no longer detects erythrocytes, produces a signal or automatically ends the retransfusion.

For the collection of the erythrocyte concentrate, it is advantageous if the lower portion of the collecting and separating container forms a funnel which tapers toward the connection with the retransfusion line.

The retransfusion line can have at least one section that can be connected to a tube pump, in order to retransfuse to the patient the erythrocyte concentrate with the necessary pressure through the microfilter, which preferably has a built-in drip chamber. This tube pump can be the same that pumps the contents of the collecting vessel into the collecting and separating container. Of course, if this pumping operation must take place continuously, a second tube pump must be connected to the retransfusion line.

A sensor can be arranged on the retransfusion tube or at the outlet of the collecting and separating container, which sensor produces an acoustic and/or visual signal or turns off the tube pump as soon as the supply of erythrocyte concentrate in the collecting and separating container is used up. If this sensor can distinguish between erythrocytes and plasma, it can render the separation of the collecting and separating containers superfluous.

BRIEF DESCRIPTION OF THE DRAWING

The invention is described in greater detail below with the aid of first and second preferred embodiments illustrated in the drawings. The single figure shows a schematic illustration of the preferred embodiment.

DETAILED DESCRIPTION OF THE PREFERRED EMBODIMENTS

Figure 1:
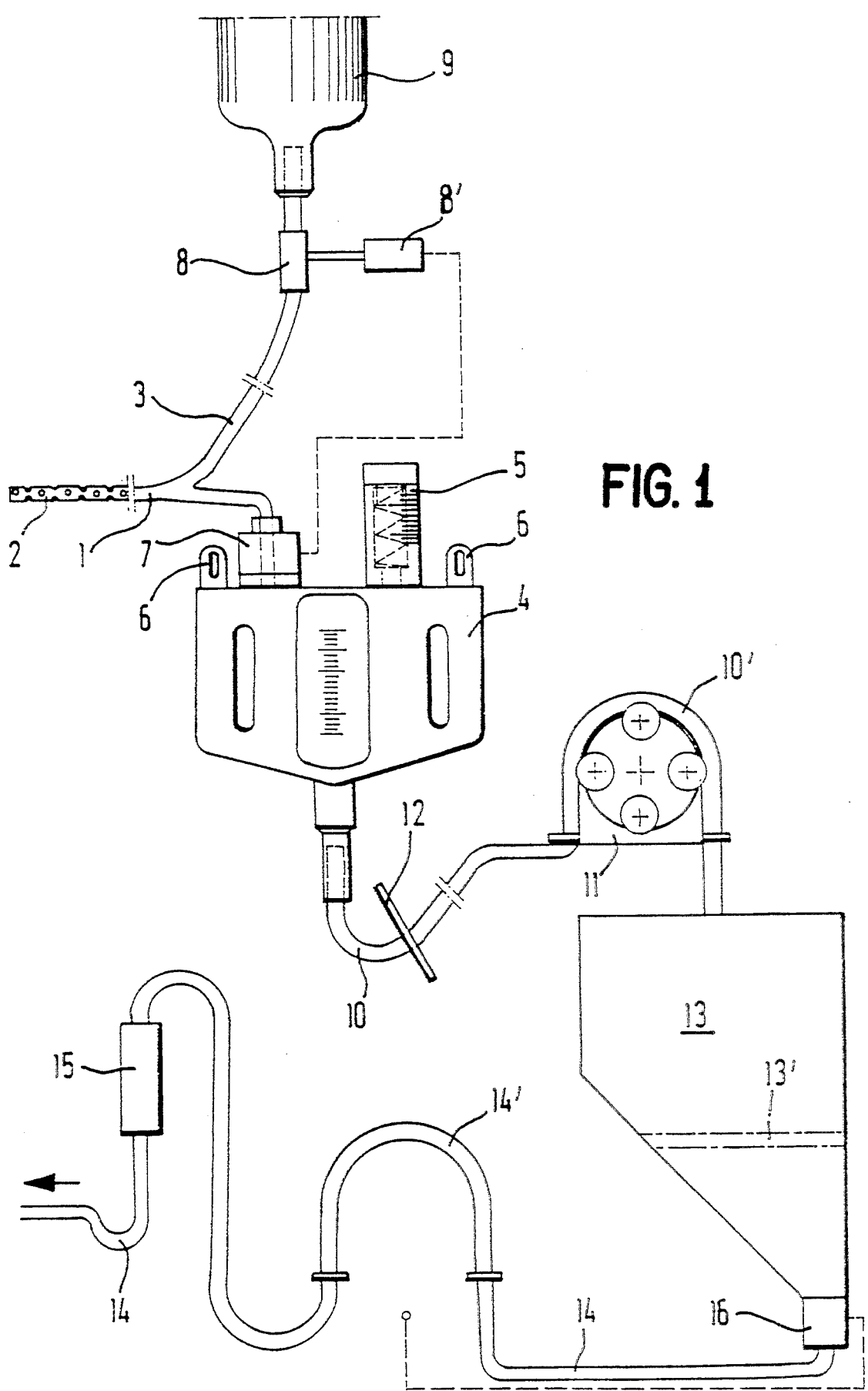
FIG. 1 shows a schematic illustration of a first preferred embodiment.
Figure 2:
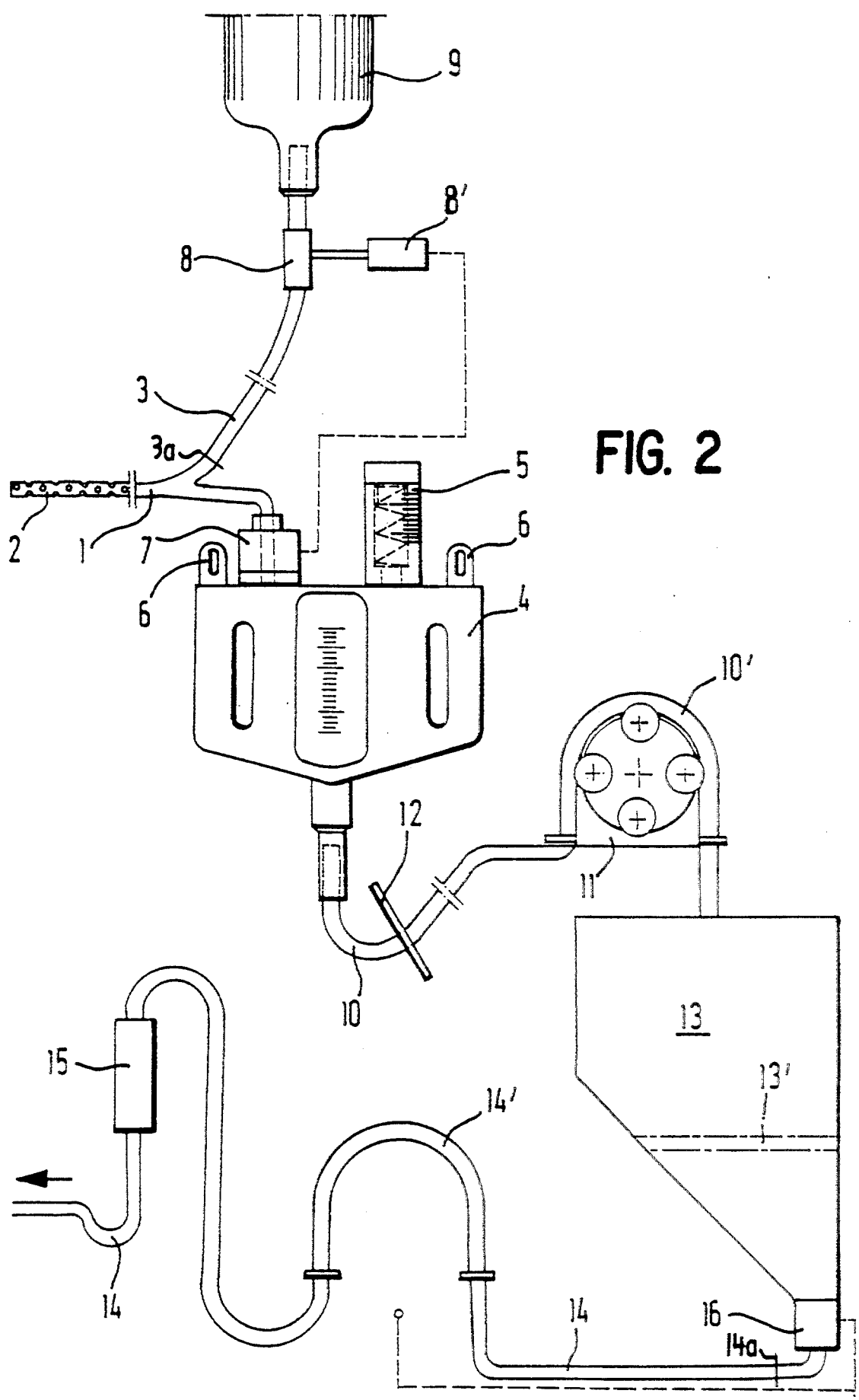
FIG. 2 shows a schematic illustration of a second preferred embodiment.

Now referring to the first preferred schematic illustration in the drawing, there is shown a closed system for collecting and retransfusing autologous blood which includes a plastic aspiration tube 1, the end section of which is formed as a drain 2. If desired, a separate drain to which the aspiration tube 1 is connected can also be provided. At a small distance from the other end of the aspiration tube 1, a branch is provided from which emanates drip tube 3, also made of plastic. The drip tube 3 can be formed in one piece with the aspiration tube 1 or be welded thereto. Additionally, the branch connection can also be produced by a separate connecting piece.

The end of the aspiration tube 1 adjacent to the branch is connected to the upper side of collecting vessel 4, preferably made of rigid plastic. A negative pressure display device (vacuum guage) 5 mounted on the upper side of the collecting vessel 4 displays the negative pressure prevailing in the collecting vessel 4 in percent of vacuum. Two eyelets 6 mounted on opposite sides of the collecting vessel 4 permit the collecting vessel 4 to be hung on a holding apparatus (not shown).

A sensor 7 is arranged at the point where the aspiration tube 1 and the collecting vessel 4 are connected. This sensor 7 detects the fluid quantity, if necessary, corrected with the proportion of the substance added to the blood, which flows through the aspiration tube 1 into the collecting vessel 4. Sensor 7 controls the actuating means 8' of a quantity dosing device 8 (via an electrical connection shown by the dashed line) which is arranged at the outlet of a dripping bottle 9 and controls the fluid quantity released by the dripping bottle 9, which is formed in a known manner, to which the drip tube 3 is connected.

At the lowermost portion of the collecting vessel 4 a tube line 10 is provided. With the exception of a section 10' which is made of a silicone rubber tube, the tube line 10 is made of plastic. A tube pump 11, also referred to as a roller pump, is positioned to be in contact with the silicone tube line 10'. The tube line 10 can be clamped between the section 10' and the collecting vessel 4 by means of a tube clamp 12.

The discharge end of the tube line 10 is connected at the top of a soft plastic collecting and separating bag 13 having separating zone 13'. The lower half of bag 13 tapers in a funnel-like manner to an outlet provided at its lower end. A retransfusion line 14 is connected to this outlet, which, like the tube line 10, has a section 14' made of silicone rubber, against which the tube pump 11 or another tube pump can be placed. Otherwise the retransfusion line 14 is made completely of plastic.

A known microfilter 15 with a drip chamber is disposed in the length of the retransfusion line 14 between the section 14' and the end to be connected with a transfusion cannula.

Sensor 16, provided at the outlet of the collecting and separating bag 13, or on the retransfusion line 14, shuts off the retransfusion pump (not shown) (via the electrical connection shown by the dashed line) when the supply of erythrocyte concentrate in the collecting and separating bag 13 is used up. Visual and/or acoustical signals can also be included in the sensor 16.

For a retransfusion, the drip bottle 9 contains an anticoagulant fluid, which is preferably mixed with a precipitation accelerating agent, such as, hydroxyethyl starch-citrate. The blood aspiration through the aspiration tube 1 into the collecting vessel 4 takes place due to the negative pressure produced here with the aid of the tube pump 11. The negative pressure can be maintained continuously at an optimum value by turning the tube pump 11 on and off, and/or by controlling its rotating speed. A vacuum adjustment determined according to the wound subjects the erythrocytes to smaller inertial forces during the aspiration, which prevents the risk of a reduction in quality of the erythrocytes due to hemolysis.

The anticoagulant—precipitation accelerating agent mixture is automatically dispensed to the blood according to the quantity detected by the sensor 7. For example, 10 parts of blood are mixed with 3 parts of a hydroxyethyl starch-citrate mixture. A good mixing is assured because the dosing takes place in the aspiration tube 1. Accordingly, there is no need to subsequently mix the blood contents in the collecting vessel 4.

A further advantage of the addition of the precipitation accelerating agent to the blood in the aspiration tube 1 before it enters the collecting vessel 4 is that the time during which the blood is in contact with foreign surfaces is very small. In this manner, an activation of clotting factors, as well as an activation of the kinin and complement systems, are at least largely avoided. As a rule, it will be advantageous in intraoperative aspiration to aspirate the blood only through the opening provided at the end of the aspiration tube 1. In this case, a sleeve (not shown) is pushed over the drain 2 to cover the openings provided in the wall of the tube. This sleeve is removed before the wound is closed.

The system according to the present invention also operates in the above-described manner in post operative aspiration if a retransfusion is to be performed. However, even if only a wound drainage is subsequently required, the system according to the invention can be used. In this case, one need only clamp, close by welding or preferably close and separate by welding the drip tube 3 by clamp or weld 3a and the retransfusion line 14 in place, by clamp or weld 14a the latter being located advantageously as close as possible to the outlet of the collecting and separating bag 13. The collecting and separating bag 13 then serves as a collecting bag for the aspirated wound secretions. It is thereby particularly advantageous that the drainage system is entirely closed. It is not necessary to exchange the collecting vessel 4 because its negative pressure can be repeatedly regenerated by means of the tube pump 11.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A system for collecting and retransfusing autologous blood produced in a wound after an operation, especially a closed wound, comprising:
    a. a collecting vessel to receive blood and anticoagulant fluid, said collecting vessel being connected to an aspiration tube in which negative pressure can be maintained;
    b. a retransfusion line containing a microfilter through which at least a portion of the blood collected in the collecting vessel is retransfused, said retransfusion line being separate from said aspiration tube;
    c. means for introducing the anticoagulant fluid into the blood before entering the collecting vessel;
    d. a bag having a separating zone for combined collecting and separating, said bag for receiving an erythrocyte concentrate, fluidly connected to said collecting vessel by means of a tube line, the outlet of said combined collecting and separating bag being fluidly connected to a retransfusion line having at least one section to which a tube pump can be applied;
    e. a sensor connected to a connection selected from a group of connections consisting of a connection located on the retransfusion line itself and a connection located on the outlet of the collecting and separating bag itself, said sensor producing a signal which shuts off the tube pump acting on the retransfusion line when the supply of erythrocyte concentrate in the collecting and separating bag is used up and said sensor produces a signal selected from the group of signals consisting of visual signals and acoustical signals;
    f. whereby, said system is closed so that the collected fluid does not contact air in the room in which the system is used.

2. System according to claim 1, wherein said means for introducing anticoagulant fluid into the blood includes a dripping bottle containing anticoagulant fluid, said dripping bottle being fluidly connected to the aspiration tube through a drip tube.

3. System according to claim 1, wherein said collecting vessel is a rigid container.

4. System according to claim 1, wherein the collecting vessel includes a negative pressure display device.

5. System according to claim 1, wherein the bag is made of a weldable plastic.

6. System according to claim 1, wherein the retransfusion line has at least one section to which a tube pump can be applied.

7. System according to claim 1, wherein the collecting and separating bag includes a separating zone having an upper portion and a lower portion, in which the upper portion to which the tube line is connected, can be tightly sealed against the lower portion, to which the retransfusion line is connected.

8. A system for collecting and retransfusing autologous blood comprising:
    a. a collecting vessel, in which a negative pressure can be maintained to receive blood and anticoagulant fluid, said collecting vessel being connected to an aspiration tube in which negative pressure can be maintained;

b. a retransfusion line to which a tube pump can be applied containing a microfilter;

c. means for introducing the anticoagulant fluid into the blood before entering the collecting vessel, said introducing means including a dripping bottle containing anticoagulant fluid, said dripping bottle being fluidly connected at an outlet to the aspiration tube through a drip tube, and a quantity dosing device located near the outlet of said dripping bottle for regulating the quantity of anticoagulant, and a sensor for producing a signal representing the quantity of incoming blood for controlling the quantity dosing device;

d. a bag having a separating zone and being fluidly connected to said collecting vessel by means of a tube line for combined collecting of blood and separating it into erythrocyte concentrate and plasma components, a part of said bag below said separating zone collecting the erythrocyte concentrate having an outlet to which said retransfusion line is connected;

e. a tube pump applied to the tube line connecting said bag with said collecting vessel for maintaining the negative pressure in said collecting vessel; and f. whereby said system is closed so that the collected fluid does not contact air in the room in which the system is used.

9. System according to claim 8, wherein said sensor means is arranged at the inlet to the collecting vessel.

10. System according to claim 9, wherein the collecting and separating bag includes a separating zone having an upper portion and a lower portion, in which the upper portion to which the tube line is connected, can be tightly sealed against the lower portion, to which the retransfusion line is connected.

11. System according to claim 9, wherein the retransfusion line has at least one section to which a tube pump can be applied.

12. System according to claim 9, wherein the collecting and separating bag is made of a weldable plastic and includes a separating zone, in which the upper portion, to which the tube line is connected, can be tightly sealed against the lower portion, to which the retransfusion line is connected by a connection, and wherein the lower portion of the collecting and separating bag forms a funnel which tapers toward the connection for the retransfusion line.

13. System according to claim 9, wherein said drip tube is joined with the aspiration tube upstream of the inlet to the collecting vessel whereby coagulant fluid is admixed with fluid in the aspiration tube prior to entering the collecting vessel.

14. System according to claim 13, wherein said merger of the drip tube and aspiration tube occurs upstream of said fluid sensor means.

15. System according to claim 14, comprising a closed system between the aspiration tube and the retransfusion line.

16. System according to claim 9, wherein said collecting vessel is a rigid container.

17. System according to claim 8, wherein the collecting and separating bag is made of a weldable plastic and includes a separating zone, in which the upper portion, to which the tube line is connected, can be tightly sealed against the lower portion, to which the retransfusion line is connected by a connection, and wherein the lower portion of the collecting and separating bag forms a funnel which tapers toward the connection for the retransfusion line.

18. System according to claim 8, wherein the collecting and separating bag includes a separating zone having an upper portion and a lower portion, in which the upper portion to which the tube line is connected, can be tightly sealed against the lower portion, to which the retransfusion line is connected.

19. System according to claim 9, wherein the retransfusion line has at least one section to which a tube pump can be applied.

20. A system for collecting and retransfusing autologous blood comprising:

a. a collecting vessel, in which a negative pressure can be maintained to receive blood and anticoagulant fluid, said collecting vessel being connected to an aspiration tube in which negative pressure can be maintained;

b. a retransfusion line to which a tube pump can be applied containing a microfilter;

c. means for introducing the anticoagulant fluid into the blood before entering the collecting vessel, said introducing means including a dripping bottle containing anticoagulant fluid, said dripping bottle being fluidly connected at an outlet to the aspiration tube through a drip tube, and a quantity dosing device located near the outlet of said dripping bottle for regulating the quantity of anticoagulant, and a sensor for producing a signal representing the quantity of incoming blood for controlling the quantity dosing device;

d. a bag having a separating zone and being fluidly connected to said collecting vessel by means of a tube line for combined collecting of blood and separating it into erythrocyte concentrate and plasma components, a part of said bag below said separating zone collecting the erythrocyte concentrate having an outlet to which said retransfusion line is connected;

e. a tube pump applied to the tube line connecting said bag with said collecting vessel for maintaining the negative pressure in said collecting vessel;

f. means for clamping located between said collecting vessel and said anticoagulant fluid introducing means; and g. means for clamping located on said retransfusion line near the outlet of said collecting and separating bag;

h. whereby, said system is closed so that the collected fluid does not contact air in the room in which the system is used.

21. A system for collecting and retransfusing autologous blood produced in a wound after an operation, especially a closed wound, comprising:

a. a collecting vessel, in which a negative pressure can be maintained to receive blood and anticoagulant fluid, said collecting vessel being connected to an aspiration tube in which negative pressure can be maintained;

b. a retransfusion line to which a tube pump can be applied containing a microfilter, said retransfusion line being separate from said aspiration tube;

c. means for introducing the anticoagulant fluid into the blood before entering the collecting vessel;

d. a bag having a separating zone and being fluidly connected to said collecting vessel by means of a tube line for combined collecting of blood and separating it into erythrocyte concentrate and plasma components, a part of said bag below said separating zone collecting the erythrocyte concentrate having an outlet to which said retransfusion line is connected, wherein the collecting and separating bag includes a separating zone having an upper portion and a lower portion, in which the upper portion to which the tube line is connected, can be tightly sealed against the lower portion, to which the retransfusion line is connected, and in which the lower portion of the collecting and separating bag forms a funnel which tapers toward the connection for the retransfusion line;

e. a tube pump applied to the tube line connecting said bag with said collecting vessel for maintaining the negative pressure in said collecting vessel; and f. whereby, said system is closed so that the collected fluid does not contact air in the room in which the system is used.

22. A system for collecting and retransfusing autologous blood produced in a wound after an operation, especially a closed wound, comprising:

a. a collecting vessel, in which a negative pressure can be maintained to receive blood and anticoagulant fluid, said collecting vessel being connected to an aspiration tube in which negative pressure can be maintained;

b. a retransfusion line to which a tube pump can be applied containing a microfilter, said retransfusion line being separate from said aspiration tube;

c. means for introducing the anticoagulant fluid into the blood before entering the collecting vessel;

d. a bag having a separating zone and being fluidly connected to said collecting vessel by means of a tube line for combined collecting of blood and separating it into erythrocyte concentrate and plasma components, a part of said bag below said separating zone collecting the erythrocyte concentrate having an outlet to which said retransfusion line is connected, wherein said bag is made of a weldable plastic and includes a separating zone, in which an upper portion, to which the tube line is connected, can be tightly sealed against a lower portion, to which the retransfusion line is connected by a connection, and wherein the lower portion of the collecting and separating bag forms a funnel which tapers toward the connection for the retransfusion line;

e. a tube pump applied to the tube line connecting said bag with said collecting vessel for maintaining the negative pressure in said collecting vessel; and f. whereby, said system is closed so that the collected fluid does not contact air in the room in which the system is used.

23. A system for collecting and retransfusing autologous blood produced in a wound after an operation, especially a closed wound, comprising:

a. a collecting vessel, in which a negative pressure can be maintained to receive blood and anticoagulant fluid, said collecting vessel being connected to an aspiration tube in which negative pressure can be maintained;

b. a retransfusion line to which a tube pump can be applied containing a microfilter, said retransfusion line being separate from said aspiration tube;

c. means for introducing the anticoagulant fluid into the blood before entering the collecting vessel, wherein said means for introducing anticoagulant fluid into the blood includes a dripping bottle containing anticoagulant fluid, said dripping bottle being fluidly connected to the aspiration tube through a drip tube;

d. a bag having a separating zone and being fluidly connected to said collecting vessel by means of a tube line for combined collecting of blood and separating it into erythrocyte concentrate and plasma components, a part of said bag below said separating zone collecting the erythrocyte concentrate having an outlet to which said retransfusion line is connected, wherein said bag is made of a weldable plastic and includes a separating zone, in which an upper portion, to which the tube line is connected, can be tightly sealed against a lower portion, to which the retransfusion line is connected by a connection, and wherein the lower portion of the collecting and separating bag forms a funnel which tapers toward the connection for the retransfusion line;

e. a tube pump applied to the tube line connecting said bag with said collecting vessel for maintaining the negative pressure in said collecting vessel; and f. whereby, said system is closed so that the collected fluid does not contact air in the room in which the system is used.

24. System according to claim 8, wherein said collecting vessel is a rigid container.

* * * * *